United States Patent [19]
Anton et al.

[11] Patent Number: 5,559,020
[45] Date of Patent: Sep. 24, 1996

[54] PROCESS FOR PREPARING GLYOXYLIC ACID/DIALKYL AMINOMETHYLPHOSPHONATE MIXTURES

[75] Inventors: David L. Anton; Robert Dicosimo, both of Wilmington, Del.

[73] Assignee: E. I. Du Pont de Nemours and Company, Wilmington, Del.

[21] Appl. No.: 385,260

[22] Filed: Feb. 8, 1995

Related U.S. Application Data

[63] Continuation-in-part of Ser. No. 67,250, May 28, 1993.

[51] Int. Cl.$^6$ .................. C12P 7/40; C12P 7/42; C12P 13/00; C07F 9/22
[52] U.S. Cl. .................. 435/136; 435/128; 435/106; 562/17
[58] Field of Search .................. 435/106, 128, 435/136; 562/17

[56] References Cited

U.S. PATENT DOCUMENTS

| | | | |
|---|---|---|---|
| 4,094,928 | 6/1978 | Gaertner | 260/944 |
| 4,882,279 | 11/1989 | Cregg | 435/172.3 |
| 4,900,668 | 2/1990 | Cooper | 435/101 |
| 5,082,778 | 1/1992 | Overbeeke et al. | 435/172.3 |
| 5,135,860 | 8/1992 | Anton et al. | 435/136 |
| 5,180,896 | 1/1993 | Anton et al. | 562/17 |

FOREIGN PATENT DOCUMENTS

| | | |
|---|---|---|
| 0186648 | 7/1986 | European Pat. Off. . |
| WO91/05868 | 5/1991 | WIPO . |
| WO93/09242 | 5/1993 | WIPO . |
| WO93/09243 | 5/1993 | WIPO . |

OTHER PUBLICATIONS

SIGMA® catalog, p. 217 (1991).
Volokita, M., et al, *J. Biological Chemistry*, 262(33), 15825–15828 (1987).
Frigerio, N. A. et al, *J. Biol. Chem.*, 231, 135–157 (1958).
Blanchard et al, *J. Biol. Chem.*, 163, 137–144 (1946).
Fry et al, *Biochimica et Biophysica Acta*, 568, 135–144 (1979).
Tolbert, N. E. et al, *J. Biol. Chem.*, 181, 905–914 (1949).
Kim et al, *Korean Biochem. J.*, 20(4), 350–356 (1987).
Clagett, C. O. et al, *J. Biol. Chem.*, 178, 977–987 (1949).
Burdick et al, *Biotechnology Letters*, 9(4), 253–258 (1987).
Urban et al, *Biochemistry*, 27, 7371–7375 (1988).
Emes et al, *Int. J. Biochem.*, 16(12), 1373–1378 (1984).
Robinson, J. C. et al, *J. of Biological Chem.*, 237(6), 2001–2010 (1962).
Richardson et al, *J. Biological Chem.*, 236(5), 1280–1284 (1961).
Zelitch et al, *J. Biol. Chem.*, 201, 707–718 (1953).

*Primary Examiner*—John W. Rollins
*Assistant Examiner*—Francisco C. Prats

[57] ABSTRACT

The invention provides a process for producing mixtures of glyoxylate and a dialkyl aminomethylphosphonate and the subsequent production of N-(phosphonomethyl)glycine, also known as glyphosate. The process comprises preparing in situ a mixture of glyoxylate and a dialkyl aminomethylphosphonate (DEAMPA) by enzymatically reacting glycolic acid (glycolate) and oxygen in an aqueous solution in the presence of a dialkyl aminomethylphosphonate and catalysts consisting of glycolate oxidase and catalase. The resulting mixture can be hydrogenated and then subjected to hydrolysis to produce N-(phosphonomethyl)glycine, a post-emergent phytotoxicant and herbicide.

4 Claims, No Drawings

PROCESS FOR PREPARING GLYOXYLIC ACID/DIALKYL AMINOMETHYLPHOSPHONATE MIXTURES

CROSS REFERENCE TO RELATED APPLICATIONS

This is a continuation-in-part of U.S. Ser. No. 08/067,250 filed May 28, 1993.

BACKGROUND OF THE INVENTION

1. Field of the Invention

This invention relates to a process for the production of mixtures of glyoxylic acid and a dialkyl aminomethylphosphonate, where glycolic acid and oxygen are reacted in an aqueous solution, in the presence of a dialkyl aminomethylphosphonate and catalysts consisting of glycolate oxidase ((S)-2-hydroxyacid oxidase, EC 1.1.3.15) and catalase (EC 1.11.1.6). The resulting mixtures of glyoxylic acid and dialkyl aminomethylphosphonate produced in this manner are useful intermediates in the production of N-(phosphonomethyl)glycine, a broad-spectrum, post-emergent phytotoxicant and herbicide useful in controlling the growth of a wide variety of plants.

2. Description of the Related Art

Glycolate oxidase, an enzyme commonly found in leafy green plants and mammalian cells, catalyzes the oxidation of glycolic acid to glyoxylic acid, with the concomitant production of hydrogen peroxide:

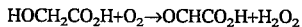

N. E. Tolbert et al., *J. Biol. Chem.*, Vol. 181, 905–914 (1949) first reported an enzyme, extracted from tobacco leaves, which catalyzed the oxidation of glycolic acid to formic acid and $CO_2$ via the intermediate formation of glyoxylic acid. The addition of certain compounds, such as ethylenediamine, limited the further oxidation of the intermediate glyoxylic acid. The oxidations were carried out at a pH of about 8, typically using glycolic acid concentrations of about 3–40 mM (millimolar). The optimum pH for the glycolme oxidation was reported to be 8.9. Oxalic acid (100 mM) was reported to inhibit the catalytic action of the glycolate oxidase. Similarly, K. E. Richardson and N. E. Tolbert, *J. Biol. Chem.*, Vol. 236, 1280–1284 (1961) showed that buffers containing tris(hydroxymethyl)aminomethane (TRIS) inhibited the formation of oxalic acid in the glycolate oxidase catalyzed oxidation of glycolic acid. C. O. Clagett, N. E. Tolbert and R. H. Burris *J. Biol. Chem.*, Vol. 178, 977–987 (1949) reported that the optimum pH for the glycolate oxidase catalyzed oxidation of glycolic acid with oxygen was about 7.8–8.6, and the optimum temperature was 35°–40° C.

I. Zelitch and S. Ochoa, *J. Biol. Chem.*, Vol. 201, 707–718 (1953), and J. C. Robinson et al., *J. Biol. Chem.*, Vol. 237, 2001–2009 (1962), reported that the formation of formic acid and $CO_2$ in the spinach glycolate oxidase-catalyzed oxidation of glycolic acid resulted from the non-enzymatic reaction of $H_2O_2$ with glyoxylic acid. They observed that addition of catalase, an enzyme that catalyzes the decomposition of $H_2O_2$, greatly improved the yields of glyoxylic acid by suppressing the formation of fonnic acid and $CO_2$. The addition of FMN (flavin mononucleotide) was also found to greatly increase the stability of the glycolate oxidase.

N. A. Frigerio and H. A. Hasbury, *J. Biol. Chem.*, Vol. 231, 135–157 (1958) have reported on the preparation and properties of glycolic acid oxidase isolated from spinach. The purified enzyme was found to be very unstable in solution; this instability was ascribed to the relatively weak binding of flavin mononucleotide (FMN) to the enzyme active site, and to the dissociation of enzymatically active tetramers and/or octamers of the enzyme to enzymatically-inactive monomers and dimers, which irreversibly aggregate and precipitate. The addition of FMN (flavin mononucleotide) to solutions of the enzyme greatly increased its stability, and high protein concentrations or high ionic strength maintained the enzyme as octamers or tetramers.

A process for the preparation of mixtures of glyoxylic acid and aminomethylphosphonic acid (AMPA) has been described in U.S. Pat. No. 5,135,860. Glycolic acid and oxygen were reacted in an aqueous solution and in the presence of AMPA and two enzyme catalysts, glycolate oxidase and catalase. This process demonstrated the synergistic effect of using both catalase (to destroy byproduct hydrogen peroxide responsible for formate production) and AMPA as an amine additive capable of forming oxidation-resistant N-substituted hemiaminal and/or imine complexes with glyoxylate (limiting its further oxidation). Yields of glyoxylic acid as high as 92% were reported, and the resulting mixtures of glyoxylic acid and AMPA were used for the preparation of N-(phosphonomethyl)glycine, a post-emergent phytotoxicant and herbicide.

SUMMARY OF THE INVENTION

This invention relates to the preparation of mixtures of glyoxylic acid and a dialkyl aminomethylphosphonate, by oxidizing glycolic acid with oxygen in aqueous solution and in the presence of a dialkyl aminomethylphosphonate and two enzyme catalysts, glycolate oxidase ((S)-2-hydroxyacid oxidase, EC 1.1.3.15) and catalase (EC 1.11.1.6). Substitution of a dialkyl aminomethylphosphonate for the previously-employed aminomethylphosphonic acid (AMPA) results in an unexpected improvement in the yield of glyoxylic acid in reactions where AMPA inhibits catalase activity. Mixtures of glyoxylic acid and a dialkyl aminomethylphosphonate are useful for the preparation of N-(phosphonomethyl)glycine, a post-emergent phytotoxicant and herbicide.

U.S. Pat. No. 5,135,860 describes a process for the preparation of mixtures of glyoxylic acid and aminomethylphosphonic acid (AMPA) using as catalysts the soluble spinach glycolate oxidase, and a soluble catalase (e.g., the soluble catalase from *Aspergillus niger*). U.S. Pat. No. 5,180,846 describes a process for the hydrogenation of these mixtures to produce N-(phosphonomethyl)glycine. A related patent application, U.S. Ser. No. 07/95 1,497, describes the preparation of glyoxylic acid/AMPA mixtures using as catalyst a genetically-engineered microbial transformant which expresses both the enzyme glycolate oxidase from spinach and an endogenous catalase. It was observed that significant quantities of formate (a product of the oxidation of glyoxylate by hydrogen peroxide) were produced when employing either a *H. polymorpha* or *P. pastoris* transformant as catalyst. The addition of a second source of catalase (e.g., soluble catalase from *Aspergillus niger*) to the reaction mixture produced high yields of glyoxylic acid when using either *H. polymorpha* or *P. pastoris* transformant catalyst.

The catalase from *Aspergillus niger*, *Aspergillus nidulans*, *Saccharomyces cerevisiae*, *Hansenula polymorpha*, *Pichia pastoris*, and bovine liver have now each been examined as catalyst for the decomposition of hydrogen peroxide generated during the oxidation of glycolate/AMPA mixtures, and a previously-unreported, reversible inhibition by AMPA of the catalase from *H. polymorpha, P. pastoris,* and bovine liver has been discovered. This inhibition occurred regardless of whether a soluble catalase, immobilized catalase, or catalase-containing whole cell catalyst was employed. As an alternative to adding an additional source of inhibition-resistant catalase to glycolate/AMPA reactions which use an AMPA-inhibited source of catalase as catalyst (e.g., *H. polymorpha* or *P. pastoris* transformants), the substitution of a dialkyl aminomethyl-phosphonate for AMPA in these same reactions has had the unexpected effect of eliminating or significantly reducing the inhibition of certain catalases which would normally occur when AMPA was employed as an amine additive.

AMPA and diethyl aminomethylphosphonate (DEAMPA) were compared as amine additives in oxidations of glycolic acid which used as catalysts soluble glycolate oxidase and either *A. niger* soluble catalase (which is not inhibited by AMPA) or *H. polymorpha* soluble catalase (inhibited by AMPA); the yields of glyoxylic acid and formic acid obtained under reaction conditions optimal for glyoxylic acid production (as described in the accompanying Examples) are listed in the table below. The yields of glyoxylic acid produced with DEAMPA were greater than those obtained with AMPA when using either *A. niger* or *H. polymorpha* soluble catalase. The improvement in glyoxylate yield at lower concentrations of *A. niger* catalase may be due to the lower $pK_a$ of the DEAMPA protonated amine ($pK_a$ ca. 6.4) when compared to AMPA ($pK_a$ 10.8); the lower $pK_a$ of DEAMPA favors the formation of oxidation resistant hemiaminal or imine complexes of unprotonated DEAMPA with glyoxylic acid at the pH at which the reactions were performed (pH 8.3–8.5).

| amine | catalase source | [catalase] (IU/mL) | glyoxylate (%) | formate (%) |
|---|---|---|---|---|
| AMPA | *A. niger* | 1,400 | 70 | 20 |
| AMPA | *A. niger* | 14,000 | 92 | 2 |
| DEAMPA | *A. niger* | 1,400 | 95 | 4 |
| DEAMPA | *A. niger* | 14,000 | 97 | 1 |
| AMPA | *H. polymorpha* | 5,600 | 43 | 45 |
| AMPA | *H. polymorpha* | 14,000 | 64 | 24 |
| AMPA | *H. polymorpha* | 56,000 | 68 | 6 |
| DEAMPA | *H. polymorpha* | 1,400 | 84 | 12 |
| DEAMPA | *H. polymorpha* | 14,000 | 98 | 1 |

Comparison of glyoxylate yields and formate production in reactions which employed either DEAMPA or AMPA and *H. polymorpha* soluble catalase (see table above) illustrates the unexpected, marked increase in glyoxylate yield and decrease in formate production when using DEAMPA as amine additive. Significantly lower concentrations of *H. polymorpha* soluble catalase could be employed to obtain high yields of glyoxylate with DEAMPA; increasing the cuncentration of this same catalase when using AMPA did not produce yields of glyoxylate comparable to those obtained with DEAMPA. Similar improvements in glyoxylate yield and decreases in fonnate production were obtained when using either *H. polymorpha* or *P. pastoris* transformants as catalyst and substituting DEAMPA for AMPA (see accompanying Examples).

DESCRIPTION OF THE PREFERRED EMBODIMENTS

The catalytic oxidation of glycolic acid is conveniently carried out by contacting the glycolic acid with a source of molecular oxygen in the presence of an enzyme catalyst which catalyzes the reaction of glycolic acid with $O_2$ to form glyoxylic acid. One such catalyst is the enzyme glycolate oxidase (EC 1.1.3.15), also known as glycolic acid oxidase. Glycolate oxidase may be isolated from numerous sources well-known to the art (supra). The glycolate oxidase used in the reaction should be present in an effective concentration, usually a concentration of about 0.01 to about 1000 IU/mL, preferably about 0.1 to about 10 IU/mL. An IU (International Unit) is defined as the amount of enzyme that will catalyze the transformation of one micromole of substrate per minute. A procedure for the assay of this enzyme is found in I. Zelitch and S. Ochoa, *J. Biol. Chem.,* Vol. 201, 707–718 (1953). This method is also used to assay the activity of recovered or recycled glycolate oxidase.

Optimal restfits in the use of glycolate oxidase as a catalyst for the oxidative conversion of glycolic acid to glyoxylic acid are obtained by incorporating into the reaction solution a catalyst for the decomposition of hydrogen peroxide. One such peroxide-destroying catalyst which is effective in combination with glycolate oxidase is the enzyme catalase (E.C. 1.11.1.6). Catalase catalyzes the decomposition of hydrogen peroxide to water and oxygen, and it is believed to improve yields of glyoxylic acid in the present process by accelerating the decomposition of the hydrogen peroxide produced as a byproduct in the glycolate oxidase-catalyzed reaction of glycolic acid with $O_2$. The concentration of catalase should be 50 to 50,000 IU/mL, preferably 2,000 to 15,000 IU/mL. It is preferred that the catalase and glycolate oxidase concentrations be adjusted within the above ranges so that the ratio (measured in IU for each enzyme) of catalase to glycolate oxidase is at least about 250:1.

In addition to using soluble enzymes as catalysts, microbial transformants which express glycolate oxidase activity as well as endogenous catalase activity have been prepared, and their use as a microbial catalyst in the present invention demonstrated. A microbial cell catalyst which has been utilized in the present invention is a transformant of *Hansenula polymorpha* (a methylotrophic yeast). Several transformants of *H. polymorpha* having sufficient glycolate oxidase activity have been prepared by inserting the DNA for glycolate oxidase into an expression vector under the control of the formate dehydrogenase (FMD) promoter. *H. polymorpha* was transformed with this vector and a strain producing high levels of glycolate oxidase was selected and designated *H. polymorpha* GO 1 and was deposited in the NRRL, Peoria, Ill. on Mar. 30, 1993, under NRRL No. Y-21065.

A more detailed description of the preparation of *H. polymorpha* cell catalysts is disclosed in PCT/US 94/07080 fried Jun. 29, 1994, which is a continuation of U.S. Ser. No. 08/085,491 filed Jul. 1, 1993, now abandoned.

*H. polymorpha* cell catalysts were typically prepared by first growing an inoculum of an *H. polymorpha* transformant in 500 mL of YPD (Difco), pH 4.4. This culture was then inoculated into a fermenter containing 10 L of Yeast Nitrogen Base (YNB, Difco) w/o amino acids (14 g), ammonium sulfate (50 g) and methanol (100 g), at pH 5.0. The fermenter was operated for 42.5 h at 37° C., an agitation rate of 400 rpm, constant pH of 5.0, 40% dissolved oxygen (controlled), and 14 psig of air. At the conclusion of the fermentation, 1.0 kg of glycerol was added and the cells harvested by centrifugation, frozen in liquid nitrogen, and stored at −80° C.

A second microbial cell catalyst which has been utilized in the present invention is a transformant of *Pichia pastoris*

(a methylotrophic yeast) which expresses the glycolate oxidase enzyme from spinach, as well as an endogenous catalase. Several transform ants of P. pastoris having sufficient glycolate oxidase activity been prepared by inserting a DNA fragment containing the spinach glycolate oxidase gene into a P. pastoris expression vector (pHIL-D4) such as to be under control of the methanol inducible alcohol oxidase I promoter, generating the plasmid pMP1. P. pastoris strain GTS 115 (NRRL Y-15851) was transformed by plasmid pMP 1 and a selection was done as to allow integration of the linearized plasmid pMP 1 into the chromosomal alcohol oxidase I locus and replacement of alcohol oxidase gene with glycolate oxidase gene. A pool of such transformants were next selected for maximal number of integrated copies of the expression cassette. A high copy number transform ant designated P. pastoris strain GS 115-MSPI was isolated and deposited in the NRRL, Peoria, Ill. on Sep. 24, 1992, under NRRL No. Y-21001. A second high copy number transformant designated P. pastoris strain MSP 12 was isolated and deposited in the NRRL, Peoria, Ill. on Dec. 28, 1992, under NRRL No. Y-21040.

P. pastoris cells were typically prepared by growing an inoculum in 100 mL of YNB containing 1% glycerol. After 48 h growth at 30° C., the cells were transferred into a fermenter containing 10L of media composed of yeast nitrogen base (YNB) w/o amino acids (134 g), glycerol (100 g), and biotin (20 mg). The fermentation was operated at pH 5.0 (controlled with NH₄OH), 30° C., agitation rate of 200 rpm, aeration of 5 slpm, 5 psig of air, and dissolved oxygen maintained at no lower than 50% saturation. When glycerol was depleted, the cells were induced to express glycolate oxidase by growth in the same media except that methanol (50 g) was substituted for glycerol. Glycolate oxidase activity during induction was followed by enzyme assay. After 24 h of induction the cells were harvested following treatment with glycerol (1 kg). Following harvest the cells were frozen in liquid nitrogen and stored at −80° C.

A more detailed description of the preparation of P. pastoris cell catalysts is disclosed in U.S. Ser. No. 08/025, 495 filed Mar. 3, 1993, now abandoned.

H. polymorpha and P. pastoris cell transformants required permeabilization prior to use as catalyst for the oxidation of glycolic acid to glyoxylic acid. A variety of known methods of permeabilization were useful for preparing cells with sufficient glycolate oxidase activity (see Felix, H. Anal. Biochemistry, Vol. 120, 211–234,(1982)). Typically, a suspension of 10 wt % wet cells in 0.1% (v/v) Triton X-100/20 mM phosphate buffer (pH 7.0) was mixed for 15 minutes, then frozen in liquid nitrogen, thawed, and washed with 20 mM phosphate/0.1 mM FMN buffer (pH 7.0). A second method of permeabilization was performed by mixing a suspension of 10 wt % wet cells in 0.2% (w/v) benzalkonium chloride/20 mM phosphate buffer (pH 7.0) for 60 minutes, then washing the permeabilized cells with 20 mM phosphate/0.1 mM FMN buffer (pH 7.0). Once permeabilized, the amount of whole cell catalyst added to a reaction mixture was chosen so as to provide the necessary concentrations of glycolate oxidase and catalase activities as described above for the corresponding soluble enzymes. Recoveries of glycolate oxidase and catalase activities of greater than 100% of their initial values are due to increased permeabilization of the whole-cell catalyst during the course of the reaction.

Microbial cell transform ants were assayed for glycolate oxidase activity by accurately weighing ca. 5–10 mg of wet cells (blotted on filter paper to remove excess moisture) into a 3-mL quartz cuvette containing a magnetic stirring bar and 2.0 mL of a solution which was 0.12 mM in 2,6-dichlorophenol-indophenol (DCIP) and 80 mM in TRIS buffer (pH 8.3). The cuvette was capped with a rubber septum and the solution deoxygenated by bubbling with nitrogen for 5 min. To the cuvette was then added by syringe 40 L of 1.0M glycolic acid/l.0M TRIS (pH 8.3), and the mixture stirred while measuring the change in absorption with time at 605 nm (8=22,000).

Catalase activity was assayed by accurately weighing ca. 2–5 mg of wet cells (blotted on filter paper to remove excess moisture) into a 3 mL quartz cuvette containing a magnetic stirring bar and 2.0 mL of distilled water, then adding 1.0 mL of 59 mM hydrogen peroxide in 50 mM phosphate buffer (pH 7.0) and measuring the change in absorption with time at 240 nm ($\epsilon$=39.4). Glycolate oxidase and catalase activities of the H. polymorpha or P. pastoris wet cells (permeabilized) cultured in different media ranged from 20–120 DCIP IU/gram wet cells for glycolate oxidase and 30,000–200,000 IU/gram wet cells for endogenous catalase.

An optional but often beneficial ingredient in the reaction mixture is flavin mononucleotide (FMN), which is generally used at a concentration of up to about 2.0 mM, preferably about 0.01 to about 0.2 mM. It is believed the FMN increases the productivity of the glycolam oxidase, by which is meant the amount of glycolic acid converted to glyoxylic acid per unit of enzyme. It is to be understood that the concentration of added FMN is in addition to any FMN present with the enzyme, because FMN is often also added to the enzyme during the preparation of the enzyme. The structure of FMN and a method for its analysis is found in K. Yagai, Methods of Biochemical Analysis, Vol. X, Interscience Publishers, New York, 1962, p. 319–355, which is hereby included by reference.

The conversion of glycolic acid to glyoxylic acid is conveniently and preferably conducted in aqueous media. Glycolic acid (2-hydroxyacetic acid) is available commercially, and in the present reaction its initial concentration is in the range of 0.10M to 2.0M, preferably between 0.25M and 1.0M. It can be used as such or as a compatible salt thereof, that is, a salt that is water-soluble and whose cation does not interfere with the desired conversion of glycolic acid to glyoxylic acid, or the subsequent reactions of the glyoxylic acid product with a dialkyl aminomethyl-phosphonate to produce N-(phosphonomethyl)glycine. Suitable and compatible salt-forming cationic groups are readily determined by trial. Representative of such salts are the alkali metal, alkaline earth metal, ammonium, substituted ammonium, phosphonium, and substituted phosphonium salts.

The dialkyl aminomethylphosphonates of the present invention have the formula

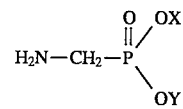

wherein X and Y are each individually alkyl groups such as methyl, ethyl, propyl, isopropyl, etc., such that the resulting dialkyl aminomethylphosphonme is partially or completely soluble in the aqueous reaction mixture. The dialkyl aminomethyl-phosphonate is added to produce a molar ratio of dialkyl methylphosphonate/glycolic acid (starting amount) in the range of from 0.01 to 3.0, preferably from 0.25 to 1.05. After combining the dialkyl aminomethyl-phosphonate and glycolic acid in an aqueous solution, the pH of the resulting mixture is adjusted to a value between 6 and 10, preferably between 7.0 and 9.0. Within is pH range, the exact value may be adjusted to obtain the desired pH by adding any compatible, non-interfering base, including alkali metal hydroxides, carbonates, bicarbonates and phosphates. The pH of the reaction mixture decreases slightly as the reaction proceeds, so it is often useful to start the reaction near the high end of the maximum enzyme activity pH range, about 9.0–8.5, and allow it to drop during the reaction. The pH can optionally be maintained by the separate addition of a non-interfering inorganic or organic buffer, since enzyme activity varies with pH.

It is understood that glycolic and glyoxylic acid are highly dissociated in water, and at pH of between 7 and 10 are largely if not entirely present as glycolate and glyoxylate ions. It will also be appreciated by those skilled in the art that glyoxylic acid (and its conjugate base, the glyoxylate anion) may also be present as the hydrate, e.g., $(HO)_2CHCOOH$ and/or as the hemiacetal, $HOOCCH(OH)OCH(OH)COOH$, which compositions and their anionic counterparts are equivalent to glyoxylic acid and its union for the present purpose of being suitable reactants for N-(phosphonomethyl)glycine formation. Similarly, the dialkyl aminomethylphosphonate may be partially or completely present as the protonated amine cation, whose counter ion may be one or more of any of the available anionic species present in the reaction mixture.

Oxygen ($O_2$), the oxidant for the conversion of the glycolic acid to glyoxylic acid, may be added as a gas to the reaction by agitation of the liquid at the gas-liquid interface or through a membrane permeable to oxygen. It is believed that under most conditions, the reaction rate is at least partially controlled by the rate at which oxygen can be dissolved into the aqueous medium. Thus, although oxygen can be added to the reaction as air, it is preferred to use a relatively pure firm of oxygen, and even use elevated pressures. Although no upper limit of oxygen pressure is known, oxygen pressures up to 50 atmospheres may be used, and an upper limit of 15 atmospheres is preferred. Agitation is important to maintaining a high oxygen dissolution (hence reaction) rate. Any convenient form of agitation is useful, such as stirring. On the other hand, as is well known to those skilled in the enzyme art, high shear agitation or agitation that produces foam may decrease the activity of soluble enzyme(s), and should be avoided when using soluble enzyme catalysts.

The reaction temperature is an important variable, in that it affects reaction rate and the stability of the enzymes. A reaction temperature of 0° C. to 40° C. may be used, but the preferred reaction temperature range is from 5° C. to 15° C. Operating in the preferred temperature range maximizes recovered enzyme activity at the end of the reaction. The temperature should not be so low that the aqueous solution starts to freeze. Temperature can be controlled by ordinary methods, such as, but not limited to, by using a jacketed reaction vessel and passing liquid of the appropriate temperature through the jacket. The reaction vessel may be constructed of any material that is inert to the reaction ingredients.

Upon completion of the reaction, soluble enzymes may be removed by filtration or centrifugation and reused. Alternatively, they can be denatured and precipitated by heating, e.g., to 70° C. for 5 minutes, and/or can be allowed to remain in the reaction mixture if their presence in the subsequent steps of converting the mixture to N-(phosphonomethyl)glycine, and of recovering N-(phosphonomethyl)glycine from the reaction mixture, is not objectionable. Microbial cell transformants may be recovered by filtration or centrifugation for recycle. Following the cessation of contacting the reaction solution with $O_2$, and preferably following the removal of the soluble enzymes or whole cell catalysts, flavin mononucleotide (FMN) may optionally be removed by contacting the solution with activated carbon.

The resulting mixtures of glyoxylic acid and dialkyl aminomethyl-phosphonate (which are believed to be in equilibrium with the corresponding hemiaminal and imine ) are treated in accordance with any of the processes known to the art for producing N-(phosphonomethyl)glycine. Catalytic hydrogenation of a mixture of glyoxylic acid and a dialkyl aminomethylphosphonate, followed by hydrolysis of the resulting N-(dialkoxyphosphinylmethyl)glycine, is a preferred method for preparing N-(phosphonomethyl)glycine from glyoxylic acid/dialkyl aminomethylphosphonate mixtures. Hydrogenation catalysts suitable for this purpose include (but are not limited to) the various platinum metals, such as iridium, osmium, rhodium, ruthenium, platinum, and palladium; also various other transition metals such as cobalt, copper, nickel and zinc. The catalyst may be unsupported, for example, as Raney nickel or platinum oxide; or it may be supported, for example, as platinum on carbon, palladium on alumina, or nickel on kieselguhr. Palladium on carbon, nickel on kieselguhr and Raney nickel are preferred. The hydrogenation can be performed at a pH of from 4 to 11, preferably from 5 to 10. The hydrogenation temperature and pressure can vary widely. The temperature is generally in the range of 0° C. to 150° C., preferably from 20° C. to 90° C., while the $H_2$ pressure is generally in the range of from about atmospheric to about 100 atmospheres, preferably from 1 to 10 atmospheres.

The N-(dialkoxyphosphinylmethyl)glycine produced via the hydrogenation of glyoxylic acid/dialkyl aminomethylphosphonate mixtures may be hydrolyzed to produce N-(phosphonomethyl)glycine by adding an excess of hydrochloric acid or hydrobromic acid to the aqueous product mixture from the hydrogenation step and heating. N-(phosphonomethyl)glycine, useful as a post-emergent herbicide, may be recovered from the resulting mixture by any of the recovery methods known to the art.

In the following examples, which serve to further illustrate the invention, the yields of glyoxylate, formate and oxalate, and the recovered yield of glycolate, are percentages based on the total amount of glycolic acid present at the beginning of the reaction. Analyses of reaction mixtures were performed by high pressure liquid chromatography (HPLC) using a Bio-Rad HPX-87H organic acid analysis column.

EXAMPLE 1

Into a 3 oz. Fischer-Porter glass aerosol reaction vessel was placed a magnetic stirring bar and 10 mL of an aqueous solution containing glycolic acid (0.25M), aminomethylphosphonic acid (AMPA, 0.263M), FMN (0.01 mM), propionic acid (HPLC internal standard, 0.125M), spinach glycolate oxidase (1.0 IU/mL), and soluble *Aspergillus niger* catalase (1,400 IU/mL) at pH 8.5. The reaction vessel was sealed and the reaction mixture was cooled to 15° C., then the vessel was flushed with oxygen by pressurizing to 70 psig and venting to atmospheric pressure five times with stirring. The vessel was then pressurized to 70 psig of oxygen and the mixture stirred at 15° C. Aliquots (0.10 mL) were removed by syringe through a sampling port (without loss of pressure in the vessel) at regular intervals for analysis by HPLC to monitor the progress of the reaction. After 5 h, the HPLC yields of glyoxylate, formate, and oxalate were 70.4%, 19.6%, and 2.2%, respectively, and 5.3% glycolate remained. The remaining activities of glycolate oxidase and catalase were 27% and 100%, respectively, of their initial values.

EXAMPLE 2

The procedure described in Example 1 was repeated using an aqueous solution containing glycolic acid (0.500M), AMPA (0.500M), FMN (0.01 mM), isobutyric acid (HPLC internal standard, 0.100M), spinach glycolate oxidase (1.0 IU/mL), and soluble *Aspergillus niger* catalase (14,000 IU/mL) at pH 8.5 and at 5° C. After 21 h, the HPLC yields of glyoxylate, formate, and oxalate were 85.2%, 1.5%, and 3.3%, respectively, and 5.5% glycolate remained. The remaining activities of glycolate oxidase and catalase were 49% and 93%, respectively, of their initial values.

EXAMPLE 3

The procedure described in Example 1 was repeated using an aqueous solution containing glycolic acid (0.500M), AMPA (0.375M), FMN (0.01 mM), isobutyric acid (HPLC internal standard, 0.100M), spinach glycolate oxidase (1.0 IU/mL), and 14,000 IU/mL of either *Aspergillus niger, Saccharomyces cerevisiae,* bovine liver, or *Hansenula polymorpha* soluble catalase at pH 8.5 and at 5° C. The reaction time, recovery of catalase and glycolate oxidase activity, and yields of glyoxylic, formic, oxalic, and glycolic acid are listed in the table below:

| soluble catalase | time (h) | catalase (%) | glycolate oxidase (%) | glyoxylic acid (%) | formic acid (%) | oxalic acid (%) | glycolic acid (%) |
|---|---|---|---|---|---|---|---|
| A. niger | 19 | 81 | 39 | 92.1 | 1.9 | 4.7 | 1.8 |
| S. cerev. | 18 | 59 | 37 | 94.2 | 2.6 | 0 | 3.0 |
| bov. liver | 18 | 34 | 27 | 40.0 | 51.4 | 2.5 | 5.3 |
| H. poly. | 19 | 75 | 46 | 64.3 | 23.7 | 4.0 | 2.7 |

EXAMPLE 4

The reaction in Example 3 was repeated at 15° C. with 14,000 IU/mL of either *Aspergillus niger* or *Hansenula polymorpha* soluble catalase. The reaction time, recovery of catalase and glycolate oxidase activity, and yields of glyoxylic, formic, oxalic, and glycolic acid are listed in the table below:

| soluble catalase | time (h) | catalase (%) | glycolate oxidase (%) | glyoxylic acid (%) | formic acid (%) | oxalic acid (%) | glycolic acid (%) |
|---|---|---|---|---|---|---|---|
| A. niger | 20 | 84 | 12 | 87.3 | 1.8 | 2.7 | 8.2 |
| H. poly. | 20 | 64 | 17 | 62.0 | 27.9 | 2.9 | 4.7 |

EXAMPLE 5

The reaction in Example 3 was repeated using 5,600 IU/mL or 56,000 IU/mL of soluble *Hansenula polymorpha* catalase. The reaction time, recovery of catalase and glycolate oxidase activity, and yields of glyoxylic, formic, oxalic, and glycolic acid for all three concentrations of catalase are listed in the table below:

| H. poly. (IU/mL) | time (h) | catalase (%) | glycolate oxidase (%) | glyoxylic acid (%) | formic acid (%) | oxalic acid (%) | glycolic acid (%) |
| --- | --- | --- | --- | --- | --- | --- | --- |
| 5,600 | 22 | 48 | 25 | 42.9 | 44.5 | 0 | 1.6 |
| 14,000 | 20 | 64 | 17 | 62.0 | 27.9 | 2.9 | 4.7 |
| 56,000 | 22 | 12 | 14 | 68.4 | 6.3 | 2.4 | 6.5 |

EXAMPLE 6

The procedure described in Example 1 was repeated using an aqueous solution containing glycolic acid (0.500M), diethyl aminomethylphosphonate (DEAMPA, 0.398M), FMN (0.01 mM), isobutyric acid (HPLC internal standard, 0.10M), spinach glycolate oxidase (1.0 IU/mL), and soluble *Aspergillus niger* catalase (14,000 IU/mL) at pH 8.3 and at 5° C. After 20 h, the HPLC yields of glyoxylate, formate, and oxalate were 97.4%, 0.8%, and 1.8%, respectively, and no glycolate remained. The remaining activities of glycolate oxidase and catalase were 10% and 95%, respectively, of their initial values.

EXAMPLE 7

The reaction in Example 6 was repeated, using an aqueous solution containing glycolic acid (0.50M), DEAMPA (0.525M), FMN (0.01 mM), isobutyric acid (HPLC internal standard, 0.10M), spinach glycolate oxidase (1.0 IU/mL), and soluble *Aspergillus niger* catalase (1,400 IU/mL) at pH 8.3. After 23 h, the HPLC yields of glyoxylate, formate, and oxalate were 95.3%, 3.9%, and 1.5%, respectively, and no glycolate remained. The remaining activities of glycolate oxidase and catalase were 12% and 100%, respectively, of their initial values.

EXAMPLE 8

The reaction in Example 7 was repeated with DEAMPA (0.525M), using 1,400 IU/mL or 14,000 IU/mL of soluble *Hansenula polymorpha* catalase. The reaction time, recovery of catalase and glycolate oxidase activity, and yields of glyoxylic, formic, oxalic, and glycolic acid are listed in the table below:

| H. poly. (IU/mL) | time (h) | catalase (%) | glycolate oxidase (%) | glyoxylic acid (%) | formic acid (%) | oxalic acid (%) | glycolic acid (%) |
| --- | --- | --- | --- | --- | --- | --- | --- |
| 1,400 | 10 | 76 | 31 | 84.2 | 11.5 | 0.6 | 2.3 |
| 14,000 | 10 | 79 | 38 | 98.2 | 1.3 | 0.4 | 2.8 |

EXAMPLE 9

Into a 3 oz. Fischer-Porter glass aerosol reaction vessel was placed a magnetic stirring bar and 10 mL of an aqueous solution containing glycolic acid (0.500M), aminomethylphosphonic acid (0.375M), isobutyric acid (0.100M, HPLC internal standard), and flavin mononucleotide (0.01 mM) at pH 8.3 (adjusted with 50% NaOH), and the solution cooled to 5° C. To the vessel was then added 0.47 g of *Hansenula polymorpha* transformant G01(10 IU glycolate oxidase and 22,100 IU catalase) which had been permeabilized by treatment with 0.1% Triton X-100/1 freeze-thaw, then the reaction vessel was sealed and the reaction mixture was cooled to 5° C. The vessel was flushed with oxygen by pressurizing to 70 psig and venting to atmospheric pressure five times with stirring, then the vessel was pressurized to 70 psig of oxygen and the mixture stirred at 5° C. Aliquots (0.10 mL) were removed by syringe through a sampling port (without loss of pressure in the vessel) at regular intervals for analysis by HPLC to monitor the progress of the reaction. After 16 h, the HPLC yields of glyoxylate, formate, and oxalate were 57.6%, 32.5%, and 2.6%, respectively, and 8.9% glycolate remained. The remaining permeabilized cell activity of glycolate oxidase and catalase were 60% and 378%, respectively, of their initial values.

EXAMPLE 10

The reaction in Example 9 was repeated, except that 14,000 IU/mL of soluble *Aspergillus niger* catalase was also added to the reaction mixture. After 16 h, the HPLC yields of glyoxylate, formate, and oxalate were 90.1%, 1.3%, and 5.9%, respectively, and 3.0% glycolate remained. The remaining activities of glycolate oxidase and catalase were 86% and 136%, respectively, of their initial values.

EXAMPLE 11

The reaction in Example 9 was repeated, substituting 0.75 g of a *Pichia pastoris* transformant MSP10 (13.2 IU glycolate oxidase and 21,200 IU catalase) which had been permeabilized by treatment with 0.1% Triton X-100/1 freeze-thaw for the *Hansenula polymorpha* transformant. After 16 h, the HPLC yields of glyoxylate, formate, and oxalate were 30.5%, 59.2%, and 10.7%, respectively, and 0.8% glycolate remained.

EXAMPLE 12

Into a 3 oz. Fischer-Porter glass aerosol reaction vessel was placed a magnetic stirring bar and 10 mL of an aqueous solution containing glycolic acid (0.500M), DEAMPA (0.525M), isobutyric acid (0.100M, HPLC internal standard), and flavin mononucleotide (0.01 mM) at pH 8.3 (adjusted with 50% NaOH), and the solution cooled to 5° C. To the vessel was then added 1.5 g of *Hansenula polymorpha* transformant G 01 (8.0 IU glycolate oxidase and 38,000 IU catalase) which had been permeabilized by treatment with 0.1% Triton X-1 00/1 freeze-thaw, then the reaction vessel was sealed and the reaction mixture was cooled to 5° C. The vessel was flushed with oxygen by pressurizing to 70 psig and venting to atmospheric pressure five times with stirring, then the vessel was pressurized to 70 psig of oxygen and the mixture stirred at 5° C. Aliquots (0.10 mL) were removed by syringe through a sampling port (without loss of pressure in the vessel) at regular intervals for analysis by HPLC to monitor the progress of the reaction. After 9 h, the HPLC yields of glyoxylate, formate, and oxalate were 98.4%, 0%, and 2.0%, respectively, and no glycolme remained. The remaining permeabilized cell activity of glycolate oxidase and catalase were 63% and 250%, respectively, of their initial values.

| amine | time (h) | catalase (%) | glycolate oxidase (%) | glyoxylic acid (%) | formic acid (%) | oxalic acid (%) | glycolic acid (%) |
|---|---|---|---|---|---|---|---|
| AMPA | 4 | 130 | 214 | 59.7 | 36.2 | 4.3 | 1.5 |
| DEAMPA | 1 | 124 | 268 | 92.9 | 3.6 | 3.9 | 0 |

EXAMPLE 13

The reaction in Example 12 was repeated., using a mixture containing glycolic acid (0.500M), AMPA (0.525M), isobutyric acid (0.100M, HPLC internal standard), flavin mononucleotide (0.01 mM), and 0.72 g of *Hansenula polymorpha* transformant G01 (43.0 IU glycolate oxidase and 39,880 IU catalase) which had been permeabilized by treatment with 0.2% benzalkonium chloride (Lonza Barquat OJ-50) at pH 8.3 (adjusted with 50% NaOH) and 5° C. After 1 h, the HPLC yields of glyoxylate, formate, and oxalate were 50.2%, 47.4%, and 1.1%, respectively, and 2.2% glycolate remained. The remaining permeabilized cell activity of glycolate oxidase and catalase were 95% and 105%, respectively, of their initial values.

EXAMPLE 14

The reaction in Example 13 was repeated using either AMPA (0.375M) or DEAMPA (0.375M) as amine additive. The reaction time, recovery of catalase and glycolate oxidase activity, and yields of glyoxylic, formic, oxalic, and glycolic acid are listed in the table below:

| amine | time (h) | catalase (%) | glycolate oxidase (%) | glyoxylic acid (%) | formic acid (%) | oxalic acid (%) | glycolic acid (%) |
|---|---|---|---|---|---|---|---|
| AMPA | 5 | 99 | 54 | 42.7 | 47.3 | 10.7 | 4.7 |
| DEAMPA | 1 | 122 | 108 | 83.5 | 15.5 | 5.6 | 0 |

EXAMPLE 15

The reaction in Example 12 was repeated, using a mixture containing glycolic acid (0.500M), either AMPA (0.375M) or DEAMPA (0.375M), isobutyric acid (0.100M, HPLC internal standard), flavin mononucleotide (0.01 mM), and 0.23 g of *Pichia pastoris* transformant GS115-MSP10 (12.3 IU glycolate oxidase and 39,420 IU catalase) which had been permeabilized by treatment with 0.2% benzalkonium chloride (Lonza Barquat OJ-50) at pH 8.3 (adjusted with 50% NaOH) and 5° C. The reaction time, recovery of catalase and glycolate oxidase activity, and yields of glyoxylic, formic, oxalic, and glycolic acid are listed in the table below:

EXAMPLE 16

The reaction in Example 15 was repeated using either AMPA (0.525M) or DEAMPA (0.525M) as amine additive. The reaction time, recovery of catalase and glycolate oxidase activity, and yields of glyoxylic, formic, oxalic, and glycolic acid are listed in the table below:

| amine | time (h) | catalase (%) | glycolate oxidase (%) | glyoxylic acid (%) | formic acid (%) | oxalic acid (%) | glycolic add (%) |
|---|---|---|---|---|---|---|---|
| AMPA | 4 | 130 | 246 | 58.2 | 34.6 | 3.6 | 1.9 |
| DEAMPA | 1 | 118 | 276 | 95.1 | 1.6 | 3.3 | 0 |

EXAMPLE 17

A mixture of glyoxylic acid (0.49M) and DEAMPA (0.525M), prepared from a mixture of glycolic acid (0.50M) and DEAMPA (0,525M) using a microbial transformant catalyst as described in Example 12, is filtered using an Amicon Centriprep 10 concentrator (10,000 molecular weight cutoff) to remove soluble proteins, mixed with 0.10 g of activated carbon to remove FMN, filtered, and the filtrate placed in a 3-oz. Fischer-Porter bottle equipped with a magnetic stirrer bar. To the bottle is then added 0.100 g of 10% Pd/C and the bottle sealed, flushed with nitrogen gas, then pressurized to 50 psig with hydrogen and stirred at 25° C. As the hydrogen pressure drops, additional hydrogen is added to maintain the pressure at 50 psig. When the hydrogen pressure remains stable, the reaction is stopped by venting the pressure and flushing with nitrogen gas. An excess of concentrated hydrochloric acid is added to the resulting aqueous solution containing N-(diethoxyphosphinylmethyl)glycine and the mixture heated to boiling, resulting in the hydrolysis of the dialkylphosphonate ester. The resulting mixture is concentrated and N-(phosphonomethyl)glycine isolated by crystallization.

Having thus described and exemplified the invention with a certain degree of particularity, it should be appreciated that the following claims are not to be so limited but are to be afforded a scope commensurate with the wording of each element of the claim and equivalents thereof.

What is claimed is:

1. In a process for reacting glycolic acid with oxygen using as catalysts the enzymes glycolate oxidase and catalase in the presence of aminomethylphosphonic acid to prepare a product mixture comprising glyoxylic acid and aminomethylphosphonic acid the improvement comprising substituting for the aminomethylphosphonic acid a dialkyl aminomethylphosphonate, wherein the corresponding alkyl groups are individually selected from methyl, ethyl, propyl and isopropyl, thereby producing a mixture of glyoxylic acid and dialkyl aminomethylphosphonate wherein the yield of glyoxylic acid is increased, said increased yield resulting from a removal of the inhibition of a catalase by aminomethylphosphonic acid.

2. The process of claim 1 wherein the resulting product mixture comprising glyoxylic acid and dialkyl aminomethylphosphonate is
   (a) reduced to the corresponding N-(dialkoxyphosphenylmethyl)glycine; and
   (b) hydrolyzed to produce N-(phosphonomethyl)glycine.

3. The process of claim 1 wherein the catalase and glycolate oxidase is in the form of a permeabilized whole microbial cell catalyst selected from the group consisting of the transformant *Hansenula polymorpha* G01 deposited under NRRL No. Y-21065 and the transformant '*Pichia pastoris*' GS115-MSP10 deposited under NRRL No. Y-21001 and '*Pichia pastoris*' MSP12 deposited under NRRL No. Y-21040 wherein the transformant expresses glycolate oxidase and catalase enzymes.

4. The process of claim 2 wherein the catalase and glycolate oxidase is in the form of the permeabilized whole microbial cell catalyst selected from the group consisting of the transformant '*Hansenula polymorpha*' G01 deposited under NRRL No. Y-21065 and the transformant '*Pichia pastoris*' GS115-MSP10 deposited under NRRL No. Y-21001 and '*Pichia pastoris*' MSP12 deposited under NRRL No. Y-21040 wherein the transformant expresses glycolate oxidase and catalase enzymes.

* * * * *